(12) United States Patent
Yanagisawa et al.

(10) Patent No.: US 9,868,097 B2
(45) Date of Patent: Jan. 16, 2018

(54) METHOD FOR REDUCING CRITICAL MICELLE CONCENTRATION, AND SURFACTANT COMPOSITION

(71) Applicants: KANEKA CORPORATION, Osaka-shi, Osaka (JP); NATIONAL INSTITUTE OF ADVANCED INDUSTRIAL SCIENCE AND TECHNOLOGY, Tokyo (JP)

(72) Inventors: Satohiro Yanagisawa, Tokyo (JP); Takuto Nagano, Osaka (JP); Masashi Izumida, Takasago (JP); Toshiaki Taira, Tsukuba (JP); Tomohiro Imura, Tsukuba (JP); Dai Kitamoto, Tsukuba (JP)

(73) Assignees: KANEKA CORPORATION, Osaka-shi, Osaka (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 15/121,630

(22) PCT Filed: Mar. 3, 2015

(86) PCT No.: PCT/JP2015/056167
§ 371 (c)(1),
(2) Date: Aug. 25, 2016

(87) PCT Pub. No.: WO2015/133455
PCT Pub. Date: Sep. 11, 2015

(65) Prior Publication Data
US 2016/0361698 A1    Dec. 15, 2016

(30) Foreign Application Priority Data

Mar. 5, 2014 (JP) .................. 2014-043060
Jun. 9, 2014 (JP) .................. 2014-118831
Jul. 28, 2014 (JP) .................. 2014-152647

(51) Int. Cl.
| | |
|---|---|
| *A61K 38/08* | (2006.01) |
| *A61K 47/00* | (2006.01) |
| *B01F 17/00* | (2006.01) |
| *A61K 8/64* | (2006.01) |
| *A61K 47/20* | (2006.01) |
| *C11D 1/10* | (2006.01) |
| *A61K 47/18* | (2017.01) |
| *A61Q 19/00* | (2006.01) |

(Continued)

(52) U.S. Cl.
CPC .............. *B01F 17/005* (2013.01); *A23L 2/52* (2013.01); *A23L 33/10* (2016.08); *A61K 8/361* (2013.01); *A61K 8/463* (2013.01); *A61K 8/466* (2013.01); *A61K 8/64* (2013.01); *A61K 8/70* (2013.01); *A61K 47/183* (2013.01); *A61K 47/20* (2013.01); *A61K 47/42* (2013.01); *A61Q 19/00* (2013.01); *B01F 17/0057* (2013.01); *B01F 17/0085* (2013.01); *C05G 3/00* (2013.01); *C09D 7/125* (2013.01); *C09D 7/1233* (2013.01); *C11D 1/008* (2013.01); *C11D 1/10* (2013.01); *C11D 1/22* (2013.01); *D21H 17/09* (2013.01); *D21H 17/20* (2013.01); *D21H 27/20* (2013.01); *A23V 2002/00* (2013.01); *A61K 2800/10* (2013.01); *A61K 2800/596* (2013.01); *A61Q 5/02* (2013.01); *A61Q 11/00* (2013.01); *A61Q 15/00* (2013.01); *A61Q 17/04* (2013.01); *A61Q 19/007* (2013.01)

(58) Field of Classification Search
CPC .................................. A61K 38/00; A61K 8/64
USPC .................................................. 514/21.8, 773
See application file for complete search history.

(56) References Cited

U.S. PATENT DOCUMENTS

2010/0062067 A1* 3/2010 Tonge ............... A61K 8/0208
424/489
2013/0072414 A1* 3/2013 Price .................... C11D 1/94
510/220

(Continued)

FOREIGN PATENT DOCUMENTS

JP  2000-327591 A  11/2000
JP  2004-27133 A   1/2004
(Continued)

OTHER PUBLICATIONS

Chen et al., "Adsorption of Sophorolipid Biosurfactants on Their Own and Mixed with Sodium Dodecyl Benzene Sulfonate, at the Air/Water Interface", Langmuir 2011, vol. 27, pp. 8854-8866.
International Search Report for PCT/JP2015/056167 dated Jun. 9, 2015.
Onaizi et al., "Micellization and interfacial behavior of a synthetic surfactant-biosurfactant mixture", Colloids and Surfaces A: Physicochem. Eng. Aspects, 2012, vol. 415, pp. 388-393.

(Continued)

*Primary Examiner* — Raymond J Henley, III
(74) *Attorney, Agent, or Firm* — Birch, Stewart, Kolasch & Birch, LLP

(57) ABSTRACT

The objective of the present invention is to provide a method for remarkably reducing a critical micelle concentration of an anionic surfactant, which is used in a large amount currently, to reduce the amount to be used. Also, the objective of the present invention is to provide a surfactant composition of which whole critical micelle concentration is remarkably reduced and in which an amount of an anionic surfactant is reduced in comparison with the case of using an anionic surfactant only as a surfactant. The method for reducing a critical micelle concentration of an anionic surfactant according to the present invention is characterized in using a cyclic lipopeptide biosurfactant in combination with the anionic surfactant.

12 Claims, 15 Drawing Sheets

(51) Int. Cl.
| | |
|---|---|
| *A23L 33/10* | (2016.01) |
| *A23L 2/52* | (2006.01) |
| *A61K 8/46* | (2006.01) |
| *A61K 47/42* | (2017.01) |
| *C05G 3/00* | (2006.01) |
| *C09D 7/12* | (2006.01) |
| *C11D 1/00* | (2006.01) |
| *C11D 1/22* | (2006.01) |
| *D21H 17/09* | (2006.01) |
| *D21H 17/20* | (2006.01) |
| *D21H 27/20* | (2006.01) |
| *A61K 8/36* | (2006.01) |
| *A61K 8/70* | (2006.01) |
| *A61Q 5/02* | (2006.01) |
| *A61Q 11/00* | (2006.01) |
| *A61Q 15/00* | (2006.01) |
| *A61Q 17/04* | (2006.01) |

(56) References Cited

U.S. PATENT DOCUMENTS

2015/0344905 A1* 12/2015 Kijlstra .............. C12N 15/8282
　　　　　　　　　　　　　　　　　　　　　　　800/301
2016/0030324 A1* 2/2016 Lu .......................... A61K 8/64
　　　　　　　　　　　　　　　　　　　　　　　424/649
2016/0046890 A1* 2/2016 Noda ...................... C11D 1/10
　　　　　　　　　　　　　　　　　　　　　　　427/322
2016/0199280 A1 7/2016 Yanagisawa et al.

FOREIGN PATENT DOCUMENTS

| JP | 2004-149446 A | 5/2004 |
|---|---|---|
| WO | WO 99/62482 A1 | 12/1999 |
| WO | WO 2015/022936 A1 | 2/2015 |

OTHER PUBLICATIONS

Sugihara et al., "A Review of Recent Studies on Aqueous Binary Mixed Surfactant Systems", Journal of Oleo Science, vol. 57, No. 2, pp. 61-92.
Written Opinion of the International Searching Authority for PCT/JP2015/056167 (PCT/ISA/237) dated Jun. 9, 2015.
Yoneda et al., "Surfactin Sodium Salt: An Excellent Bio-Surfactant for Cosmetics", Journal of Cosmetic Science, 2001, vol. 52, No. 2, pp. 153-154.
Yoneda et al., Surfactin Sodium Salt: An Excellent Bio-Surfactant for Cosmetics, Fragrance Journal, 2001, vol. 29, No. 12, pp. 93-97.
Yoshida et al., "Shin-ban Kaimen-Kassei-Zai Handobukku (New Edition, Surfactant Handbook)", published by Kogaku Tosho Co., pp. 135-136 (1987).
Extended European Search Report dated Jul. 25, 2017 for European Application No. 15757734.7.

* cited by examiner

METHOD FOR REDUCING CRITICAL MICELLE CONCENTRATION, AND SURFACTANT COMPOSITION

TECHNICAL FIELD

The present invention relates to a method for reducing a critical micelle concentration of an anionic surfactant, and a surfactant composition in which a critical micelle concentration of an anionic surfactant is reduced.

BACKGROUND ART

It has been known that a surfactant has both of a hydrophilic part and a lipophilic part in one molecule, and exhibits various activities such as wash, dispersion, antirust, anticorrosive, moistening, penetration, bubble formation, emulsifying, solubilization and antistat. A surfactant is used for emulsifying and dispersing an insoluble component in water by utilizing the above-described activities in a various use such as a cosmetic product, a pharmaceutical product and an ink.

For example, a surfactant exhibits the function by forming an aggregate of molecules thereof in water and enclosing a lipophilic component in the aggregate. In order to form such an aggregate, it is necessary to adjust the concentration of a surfactant to a certain level. The minimum concentration of a surfactant to form the aggregate is referred to as CMC: critical micelle concentration. Each surfactant has a particular CMC value.

In general, it is preferred that an amount of a surfactant to be used is small in terms of environmental impact and economic efficiency. For example, a synthetic surfactant such as sodium linear alkylbenzene sulfonate and sodium dodecyl sulfate is utilized for various products and uses, since a synthetic surfactant can be inexpensively produced. However, a surfactant may cause various environmental damage, since a surfactant has a function to homogenize a hydrophilic component and a lipophilic component. It is therefore preferred to reduce an amount of a surfactant to be used as much as possible and not to release a surfactant to the environment. In addition, a certain surfactant, particularly a synthetic anionic surfactant, easily penetrates dermal tissue and mucous membrane to give harm to a living body. Accordingly, a surfactant having lower critical micelle concentration is considered to be better one, since such a surfactant fulfills a function even in a lower concentration and may be blended to be a composition more freely.

Thus, a surfactant which exhibits low critical micelle concentration has been developed, and it has also been studied that whole critical micelle concentration is reduced by using a plurality of surfactants. For example, it is described in Non-patent Document 1 that critical micelle concentration is reduced by mixing sophorolipid and sodium dodecylbenzenesulfonate in comparison with the case of sodium dodecylbenzenesulfonate only. Sophorolipid is one kind of biosurfactant, which is a natural surfactant produced by microorganism.

It is described in Non-patent Document 2 that the critical micelle concentration of sodium dodecyl sulfate may be changed by mixing sodium dodecyl sulfate with a long-chain alkanoyl-N-methylglucamide, i.e. MEGA-8 to MEGA-10.

It is described in Non-patent Document 3 that a plurality of surfactants are mixed to be used.

PRIOR ART DOCUMENT

Non-Patent Document

Non-patent Document 1: Minglei Chen et al., Langmuir, 27, pp. 8854-8866 (2011)
Non-patent Document 2: Gohsuke Sugihara et al., J. Oleo Sci., 57(2), pp. 61-92 (2008)
Non-patent Document 3: Tokiyuki Yoshida et al., "Shinban Kaimen-Kassei-Zai Handobukku (New Edition, Surfactant Handbook" published by Kogaku Tosho Co., p. 135-136 (1987)

DISCLOSURE OF THE INVENTION

Problems to be Solved by the Invention

As described above, it has been studied that whole critical micelle concentration is reduced by using a plurality of surfactants.

However, as the data described in Non-patent Document 3, even when a plurality of surfactants are mixed to be used, the critical micelle concentration may be decreased or increased and at least, cannot be remarkably decreased. In addition, though Non-patent Document 2 discloses the combination of sodium dodecyl sulfate as a representative synthetic anionic surfactant and n-alkanoyl-N-methylglucamide (MEGA) as a non-ionic surfactant, the effect to reduce the critical micelle concentration by the combination is not so good. Furthermore, even when sophorolipid as a biosurfactant is added to a synthetic anionic surfactant according to the technique described in Non-patent Document 1, the remarkable effect to reduce a critical micelle concentration could not be obtained.

Under the above-described circumstances, the objective of the present invention is to provide a method for remarkably reducing a critical micelle concentration of an anionic surfactant, which is used in a large amount currently, to reduce the amount to be used. Also, the objective of the present invention is to provide a surfactant composition of which whole critical micelle concentration is remarkably reduced and in which an amount of an anionic surfactant is reduced in comparison with the case of using an anionic surfactant only as a surfactant.

Means for Solving the Problems

The inventors of the present invention made extensive studies to solve the above problems. As a result, the inventors completed the present invention by finding that when a cyclic lipopeptide biosurfactant having a bulky structure is used in combination, whole critical micelle concentration can be remarkably reduced and an amount of an anionic surfactant to be used can be reduced in comparison with the case of using an anionic surfactant only.

Hereinafter, the present invention is described.

[1] A method for reducing a critical micelle concentration of an anionic surfactant, comprising the step of using a cyclic lipopeptide biosurfactant in combination with the anionic surfactant.

[2] The method according to the above [1], wherein surfactin represented by the following formula (I) or a salt thereof is used as the cyclic lipopeptide biosurfactant:

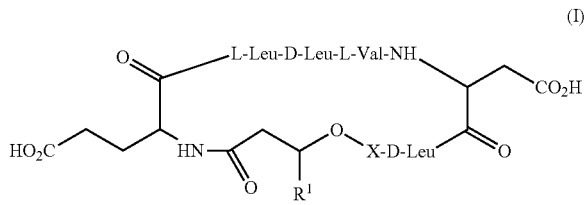

wherein 'X' is a residue of amino acid selected from leucine, isoleucine and valine; and $R^1$ is a $C_{9-18}$ alkyl group.

[3] The method according to the above [1] or [2], wherein a linear alkylbenzene sulfonate, an alfa-olefin sulfonate or an alkyl sulfate is used as the anionic surfactant.

[4] The method according to any one of the above [1] to [3], wherein the cyclic lipopeptide biosurfactant is used in a ratio of 0.1 mol % or more to a total of the anionic surfactant and the cyclic lipopeptide biosurfactant.

[5] A surfactant composition, comprising an anionic surfactant and a cyclic lipopeptide biosurfactant.

[6] The surfactant composition according to the above [5], wherein the cyclic lipopeptide biosurfactant is surfactin represented by the following formula (I) or a salt thereof:

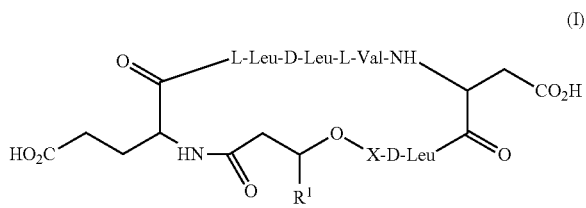

wherein 'X' is a residue of amino acid selected from leucine, isoleucine and valine; and $R^1$ is a $C_{9-18}$ alkyl group.

[7] The surfactant composition according to the above [5] or [6], wherein the anionic surfactant is a linear alkylbenzene sulfonate, an alfa-olefin sulfonate or an alkyl sulfate.

[8] The surfactant composition according to any one of the above [5] to [7], comprising the cyclic lipopeptide biosurfactant in a ratio of 0.1 mol % or more to a total of the anionic surfactant and the cyclic lipopeptide biosurfactant.

[9] The surfactant composition according to any one of the above [5] to [8], further comprising water.

[10] Use of a cyclic lipopeptide biosurfactant for reducing a critical micelle concentration of an anionic surfactant.

[11] The use according to the above [10], wherein the cyclic lipopeptide biosurfactant is surfactin represented by the following formula (I) or a salt thereof:

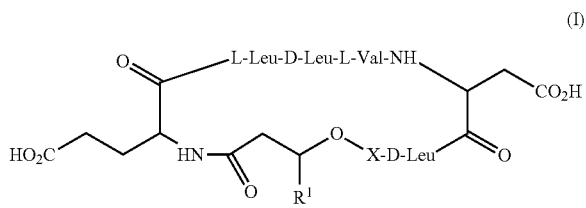

wherein 'X' is a residue of amino acid selected from leucine, isoleucine and valine; and $R^1$ is a $C_{9-18}$ alkyl group.

[12] The use according to the above [10] or [11], wherein the anionic surfactant is a linear alkylbenzene sulfonate, an alfa-olefin sulfonate or an alkyl sulfate.

[13] The use according to any one of the above [10] to [12], wherein the cyclic lipopeptide biosurfactant is used in a ratio of 0.1 mol % or more to a total of the anionic surfactant and the cyclic lipopeptide biosurfactant.

Effect of the Invention

There has been concerned that an anionic surfactant give harm to a living body and the environment, but an anionic surfactant has been used in a large amount since an anionic surfactant can be easily produced and is inexpensive. On the one hand, according to the present invention, a critical micelle concentration of an anionic surfactant can be remarkably reduced. It therefore become possible by the present invention to reduce an amount of an anionic surfactant to be used. In addition, the cyclic lipopeptide biosurfactant used in the present invention is a peptide compound; therefore, is very safe for a living body and the environment. The present invention is therefore extremely useful for industries, since the present invention can overcome a drawback of an anionic surfactant.

(1) is a AFM image of a SUS base material treated by 25 ppm aqueous solution of SFNa, (2) is a AFM image of a SUS base material treated by 12.5 ppm aqueous solution of SFNa, and (3) is a AFM image of a SUS base material treated by 8 ppm aqueous solution of SFNa.

Figure 11:
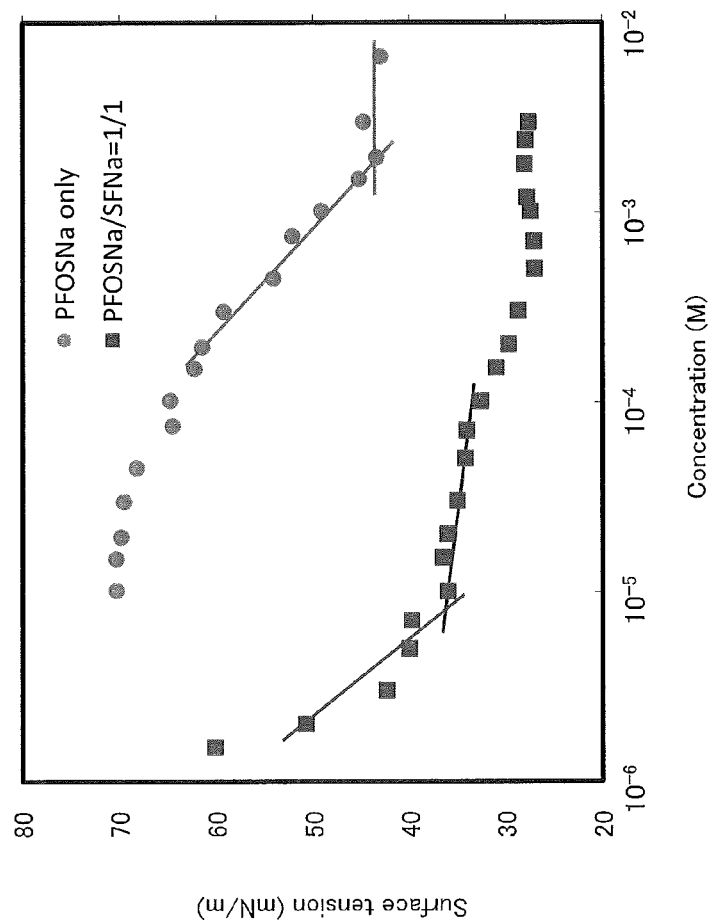

FIG. 11 is a graph to demonstrate the measurement results of the surface tensions of an aqueous solution of sodium perfluorooctanoate (PFOSNa) only, and an aqueous solution of PFOSNa and surfactin sodium salt (SFNa) in a molar ratio of 1:1, in other words, an aqueous solution containing 50 mol % of SFNa to the total of PFOSNa and SFNa.

Figure 12:
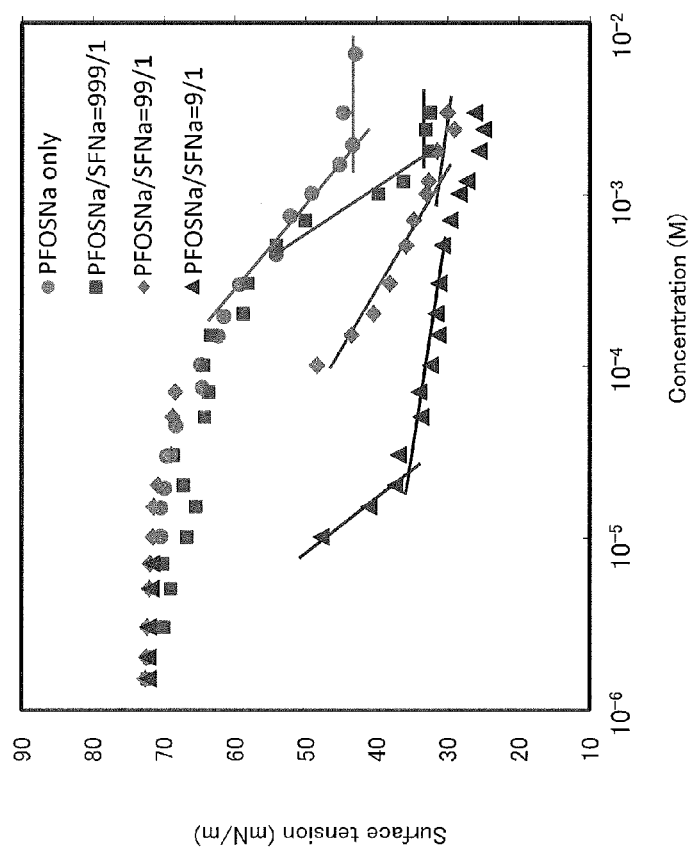

FIG. 12 is a graph to demonstrate the measurement results of the surface tensions of an aqueous solution of PFOSNa only, and aqueous solutions prepared by adding SFNa in a molar ratio of 9:1 (10 mol %), 99:1 (1 mol %) and 999:1 (0.1 mol %) to PFOSNa.

Figure 13:
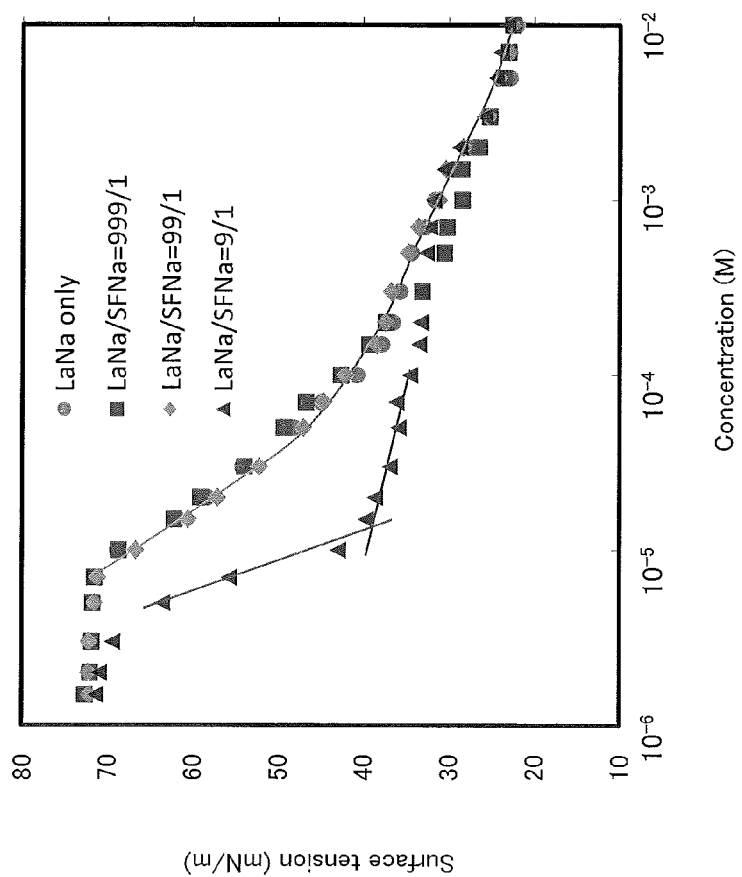

FIG. 13 is a graph to demonstrate the measurement results of the surface tensions of an aqueous solution of LaNa only, and aqueous solutions prepared by adding SFNa in a molar ratio of 9:1 (10 mol %), 99:1 (1 mol %) and 999:1 (0.1 mol %) to LaNa.

Figure 14:
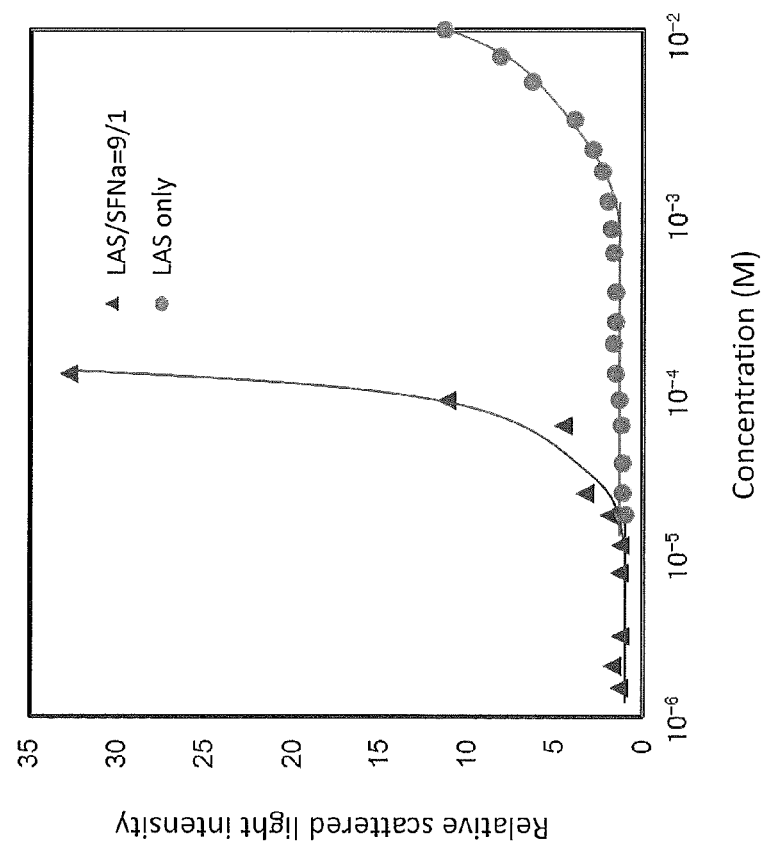

FIG. 14 is a graph to demonstrate the measurement results of the concentration-dependent relative scattered light intensity of an aqueous solution of LAS only, and an aqueous solution prepared by adding SFNa in a molar ratio of 9:1 (10 mol %) to LAS.

Figure 15:
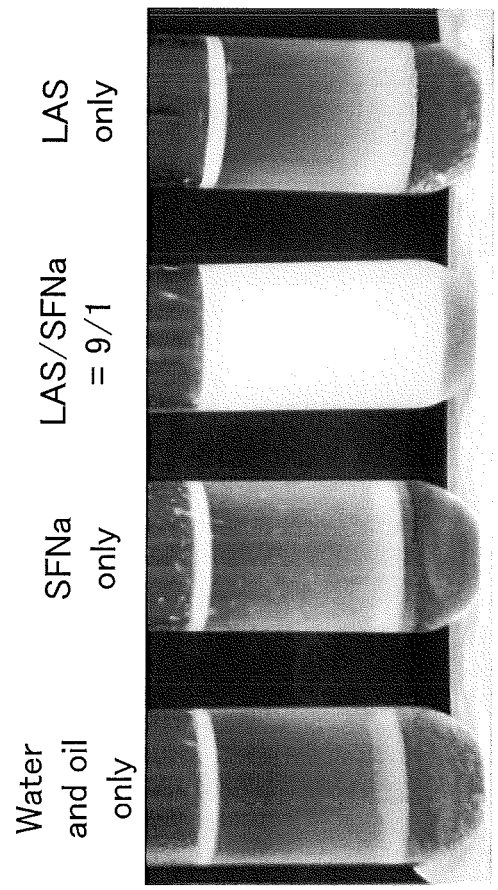

FIG. 15 represents the visually observed results of emulsions prepared by adding LAS only, SFNa only, and SFNa in a molar ratio of 9:1 (10 mol %) to LAS in 1 mL of water and 3 mL of squalane.

MODE FOR CARRYING OUT THE INVENTION

According to the present invention method, a critical micelle concentration of an anionic surfactant is reduced by combining a cyclic lipopeptide biosurfactant with the anionic surfactant. The surfactant composition of the present invention comprises an anionic surfactant and a cyclic lipopeptide biosurfactant. Hereinafter, each component used in the present invention is described first.

In the present invention, the term "anionic surfactant" means a surfactant which has an anion group as a hydrophilic group. However, some cyclic lipopeptide biosurfactant which is other important component of the present invention may be anionic and considered to be an anionic surfactant. In such a case, the cyclic lipopeptide biosurfactant which is other important component of the present invention is regarded as being different from the cyclic lipopeptide biosurfactant which is also considered to be the anionic surfactant.

An anionic surfactant may be a naturally occurring surfactant and a synthetic surfactant, which is chemically synthesized. Such a naturally occurring surfactant is exemplified by a long-chain fatty acid and a biosurfactant having a negative group such as carboxy group. Many of such a synthetic anionic surfactant is contained in a so-called synthetic detergent, and exemplified by a linear alkylbenzene sulfonate (LAS), an alfa-olefin sulfonate (AOS), an alkyl sulfate (AS), a sodium alkylether sulfate (AES), an alkyl phosphate (MAP), a polyoxyethylene alkyl ether phosphate and a polyoxyethylene alkyl phenyl ether phosphate.

A linear alkylbenzene sulfonate (LAS) is a surfactant having a structure in which a linear alkylbenzene as a hydrophobic part is substituted by a sulfonate salt group. LAS is consumed in a large amount on behalf of a branched alkylbenzene sulfonate (ABS), since pollution by bubbles due to ABS became a problem. However, LAS has a bad influence on a human body and the environment. For example, LAS causes skin problems. It is therefore required to reduce an amount of LAS to be used. LAS is exemplified by sodium dodecylbenzenesulfonate.

An alfa-olefin sulfonate (AOS) is a surfactant having a structure in which a linear alkyl group as a hydrophobic part is substituted by a sulfonate salt group. AOS has good biodegradability; however, it is said that AOS has the highest toxicity to fishes among surfactants. It is therefore required to reduce an amount of AOS to be used. AOS is exemplified by sodium 1-tetradecenesulfonate, sodium hexadecenesulfonate, sodium 3-hydroxyhexadecyl-1-sulfonate, sodium octadecene-1-sulfonate and sodium 3-hydroxy-1-octadecenesulfonate.

An alkyl sulfate (AS) is a salt of an ester of a higher alcohol and sulfuric acid. AS is incorporated into a dish detergent, shampoo, dentifrice or the like, since AS has weaker protein denaturation effect than LAS and has high biodegradability behind a higher fatty acid salt, i.e. soap. However, AS may be harmful and is used for a use of making a contact with the skin or the mucosa. It is therefore required to reduce an amount of AS to be used all the same. AS is exemplified by sodium dodecyl sulfate.

A sodium alkylether sulfate (AES) has a structure in which there is a polyalkylene glycol chain between an alkyl group and a sulfate salt group of AS. It is particularly required to reduce an amount of AES to be used, since it is known that AES causes skin problems behind LAS and further it is reported that AES increases embryo absorption, decreases pregnancy rate, inhibits implantation of a fertilized egg, or the like. The term "embryo absorption" means that embryo dies within the uterus during pregnancy and is absorbed in the placenta.

Since a surfactant which contains a phosphate salt group, such as an alkyl phosphate (MAP), a polyoxyethylene alkyl ether phosphate and a polyoxyethylene alkyl phenyl ether phosphate, causes eutrophication of lake or the like, an amount thereof to be used should be reduced.

A counter cation which constitutes an anionic surfactant is exemplified by a potassium ion and an ammonium ion in addition to a sodium ion.

In addition, there is a problem that a naturally occurring long-chain fatty acid salt must be used in a larger amount in order to obtain a similar effect to a synthetic anionic surfactant, since in general, a critical micelle concentration thereof is relatively higher than that of a synthetic anionic surfactant.

In the present invention, only one anionic surfactant may be used, or two or more anionic surfactants may be combined to be used.

As described above, an anionic surfactant causes some sort of trouble. On the one hand, according to the present invention, a critical micelle concentration of an anionic surfactant can be remarkably reduced and an amount thereof to be used can be reduced by using a cyclic lipopeptide biosurfactant in combination. In the present invention, a synthetic anionic surfactant is preferably used as an anionic surfactant, since it is particularly required that an amount of a synthetic anionic surfactant to be used is reduced.

A cyclic lipopeptide biosurfactant is a cyclic peptide which has a lipophilic group such as a long-chain alkyl group and which has a surface active function. A cyclic lipopeptide biosurfactant may be cationic when the biosurfactant contains many basic amino acids. However, a cyclic lipopeptide biosurfactant which has been found has a negative group such as carboxy group and is anionic. In addition, when an anionic surfactant is used in combination with a cationic surfactant, an insoluble substance is generated and a surface active action cannot be obtained. It is therefore preferred that the cyclic lipopeptide biosurfactant according to the present invention is anionic.

In the present invention, a cyclic lipopeptide biosurfactant is used in addition to an anionic surfactant in combination. As a result, according to the experimental knowledge by the present inventors, a critical micelle concentration of an anionic surfactant can be reduced to about ¹⁄₁₀₀₀ in some cases, though a result is dependent on an amount of a cyclic lipopeptide biosurfactant to be mixed. Although the reason is not necessarily clear, it is considered that a cyclic lipopeptide biosurfactant forms micelle with an anionic surfactant when the biosurfactant enters anionic surfactant molecules to reduce the minimum amount of the anionic surfactant required for the formation of the micelle, since a cyclic lipopeptide biosurfactant is very bulky and easy to be arrayed due to the cyclic structure thereof. In addition, a cyclic lipopeptide biosurfactant is extremely high in biodegradability and gives only a little influence on a living body and the environment, since the biosurfactant is a peptide compound.

A cyclic lipopeptide biosurfactant has a molecular structure in which a cyclic peptide part is bulky, and the occupancy area thereof per one molecular is broad. In other words, a small amount of the biosurfactant molecule can cover a surface of a solid. In addition, when the solution thereof is merely cast on a base material, the biosurfactant forms a lamella structure to be a thick coat, since the surface orientation property of the biosurfactant is excellent. As a result, high antirust effect and antistatic effect may be possibly obtained.

A cyclic lipopeptide biosurfactant is not particularly restricted as long as the biosurfactant has a bulky cyclic structure and is a peptide compound having a surface active function, and is exemplified by surfactin, arthrofactin, lichenysin and viscosin.

In the present invention, surfaction (I) or a salt thereof is preferably used as the cyclic lipopeptide biosurfactant.

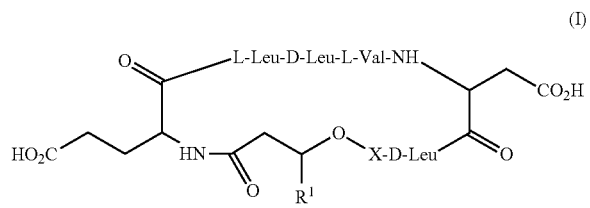

(I)

wherein 'X' is a residue of amino acid selected from leucine, isoleucine and valine; $R^1$ is a $C_{9-18}$ alkyl group.

Although the amino acid residue as 'X' may be in either a L-form or a D-form, the L-form is preferred.

The term "$C_{9-18}$ alkyl group" means a linear or branched monovalent saturated hydrocarbon group having 9 or more and 18 or less carbon atoms. The example thereof includes n-nonyl, 6-methyloctyl, 7-methyloctyl, n-decyl, 8-methylnonyl, n-undecyl, 9-methyldecyl, n-dodecyl, 10-methylundecyl, n-tridecyl, 11-methyldodecyl, n-tetradecyl, n-pentadecyl, n-hexadecyl, n-heptadecyl and n-octadecyl.

In the present invention, either one of the cyclic lipopeptide biosurfactant may be used, or two or more cyclic lipopeptide biosurfactants may be combined to be used. For example, two or more surfactin (I) of which $C_{9-18}$ alkyl groups are different may be used.

A cyclic lipopeptide biosurfactant can be obtained by a conventionally known method. For example, surfactin (I) can be isolated from a culture broth prepared by cultivating a microorganism such as a strain belonging to *Bacillus subtilis* in accordance with a known method. The surfactin (I) may be a purified product or an unpurified product. For example, a culture broth may be directly used as the unpurified product. Alternatively, the product of the cyclic lipopeptide biosurfactant obtained by a chemical synthesis method may be similarly used.

The counter cation which constitutes the salt of the anionic cyclic lipopeptide biosurfactant is not particularly restricted and exemplified by an alkali metal ion and an ammonium ion.

An alkali metal ion for the salt of the anionic cyclic lipopeptide biosurfactant is not particularly restricted and exemplified by a lithium ion, a sodium ion, a potassium ion or the like. When two or more alkali metal ions are used, the ions may be the same as or different from each other.

The example of a substituent of the ammonium ion includes an organic group, for example, an alkyl group such as methyl, ethyl, n-propyl, isopropyl, n-butyl and t-butyl; an aralkyl group such as benzyl, methylbenzyl and phenylethyl; and an aryl group such as phenyl, toluyl and xylyl. The ammonium ion is exemplified by a tetramethylammonium ion, a tetraethylammonium ion and a pyridinium ion.

In the salt of the anionic lipopeptide biosurfactant, two counter cations may be the same as or different from each other. In addition, when the cyclic lipopeptide biosurfactant has two or more carboxy groups as surfaction (I), a part of the carboxy groups may be in the state of —COOH or —COO⁻.

The ratio of an anionic surfactant and a cyclic lipopeptide biosurfactant to be used may be appropriately adjusted depending on the kind of the anionic surfactant or the like. For example, according to the experimental knowledge by the present inventors, when 0.1 mol % of a cyclic lipopeptide biosurfactant was added to a total of a linear alkylbenzene sulfonate (LAS) and the cyclic lipopeptide biosurfactant, the critical micelle concentration of LAS could not be reduced. However, when 0.1 mol % of a cyclic lipopeptide biosurfactant was added to a total of SDS as an alkyl sulfate (AS) and the cyclic lipopeptide biosurfactant, the critical micelle concentration of SDS could be sufficiently reduced. Specifically, the ratio of an anionic surfactant and a cyclic lipopeptide biosurfactant to be used may be determined by a preliminary experiment or the like depending on a target reduction degree of critical micelle concentration.

In general, the ratio of a cyclic lipopeptide biosurfactant to a total of an anionic surfactant and the cyclic lipopeptide biosurfactant may be adjusted to 0.1 mol % or more, and is preferably 0.5 mol % or more, more preferably 1 mol % or more, even more preferably 5 mol % or more, and particularly preferably 10 mol % or more. On the one hand, the upper limit of the ratio is not particularly restricted, and the ratio is preferably 70 mol % or less, more preferably 60 mol % or less, and even more preferably 50 mol % or less, in terms of a cost, since a cyclic lipopeptide biosurfactant is generally more expensive than an anionic surfactant.

In the present invention, a critical micelle concentration of an anionic surfactant is reduced by using a cyclic lipopeptide biosurfactant in combination with the anionic surfactant. In other words, the method for reducing a critical micelle concentration of an anionic surfactant according to the present invention is characterized in comprising the step of using a cyclic lipopeptide biosurfactant in combination with the above-described anionic surfactant. Thus, the surfactant composition according to the present invention may consist of an anionic surfactant and a cyclic lipopeptide biosurfactant only.

Alternatively, the surfactant composition according to the present invention may contain a component other than an anionic surfactant and a cyclic lipopeptide biosurfactant. For example, the composition may contain water as a medium. In addition, the composition may further contain a water-miscible organic solvent such as ethanol.

Other component contained in the surfactant composition according to the present invention is not particularly restricted and may be appropriately selected depending on the form of a final product or the like. The other component is exemplified by a polysaccharide thickener such as guar gum and xanthane gum; a cellulose compound such as hydroxypropyl cellulose and carboxymethyl cellulose; a carboxyvinyl polymer such as an acrylic acid polymer and an acrylic acid copolymer; a silicone compound; a colorant; a pH adjuster; a plant extract; a preservative; a chelating agent; a vitamin preparation; a medicinal ingredient such as an anti-inflammatory drug; a fragrance; a ultraviolet absorber; an antioxidant; or the like.

The final form of the surfactant composition according to the present invention is not particularly restricted, and exemplified by a cosmetic product and a toiletry product, such as cream, gel, lotion, shampoo, a shower and bath product, a deodorant product, an anhidrotic, a sunscreen product, an ornamental product, a liquid dentifrice and a mouth rinse; a wet wiper such as wet tissue, which is used as a makeup remover and for wiping the buttocks of a baby; a medical or domestic antiseptic solution for maniphalanx or the like; a textile product; an oil solution for a textile product; an emulsifier used for a gum product and a plastic product and used in the production process thereof; a detergent, an antirust agent and a surface preparation agent used for a civil engineering product and an architecture product and for washing and processing the products; a paper product and a pulp product; a machine product and a metal product; a cleaning product; a beverage and a food; a paint product and an ink product; a product for environmental conservation; an agricultural product and a fertilizer product; an information industry product; an antistat; a surface preparation agent; other industrial detergent; and the like.

The present application claims the benefit of the priority dates of Japanese patent application No. 2014-43060 filed on Mar. 5, 2014, Japanese patent application No. 2014-118831 filed on Jun. 9, 2014, and Japanese patent application No. 2014-152647 filed on Jul. 28, 2014. All of the contents of the Japanese patent application No. 2014-43060 filed on Mar. 5, 2014, Japanese patent application No. 2014-118831 filed on Jun. 9, 2014, and Japanese patent application No. 2014-152647 filed on Jul. 28, 2014, are incorporated by reference herein.

EXAMPLES

Hereinafter, the present invention is described in more detail with Examples. However, the present invention is not restricted to the following Examples in any way, and it is possible to work the present invention according to the Examples with an additional appropriate change within the range of the above descriptions and the following descriptions. Such a changed embodiment is also included in the technical scope of the present invention.

Example 1: Effect to Reduce Amount of Sodium Linear Alkylbenzene Sulfonate to be Used by Surfactin Sodium Salt The effect to reduce the amount of a sodium linear alkylbenzene sulfonate (LAS) to be used by surfactin sodium salt (SFNa) was evaluated by surface tension measurement. LAS is a major anionic surfactant of a detergent. Specifically, first, LAS or SFNa and ultrapure water were added into a vial container, and LAS or SFNa was dissolved by stirring with a stirrer to prepare 10 mM aqueous solution. The solutions were mixed at a prescribed ratio. The mixed solutions were diluted by further adding ultrapure water to obtain test aqueous solutions. Each of the aqueous solution was added into a petri dish and left to stand still all night and all day. Then, the concentration dependency of the surface tension was evaluated at 25° C. using a high-performance surface tension meter ("DY-500" manufactured by Kyowa Interface Science Co., Ltd.). The result is shown in FIG. 1.

Figure 1:
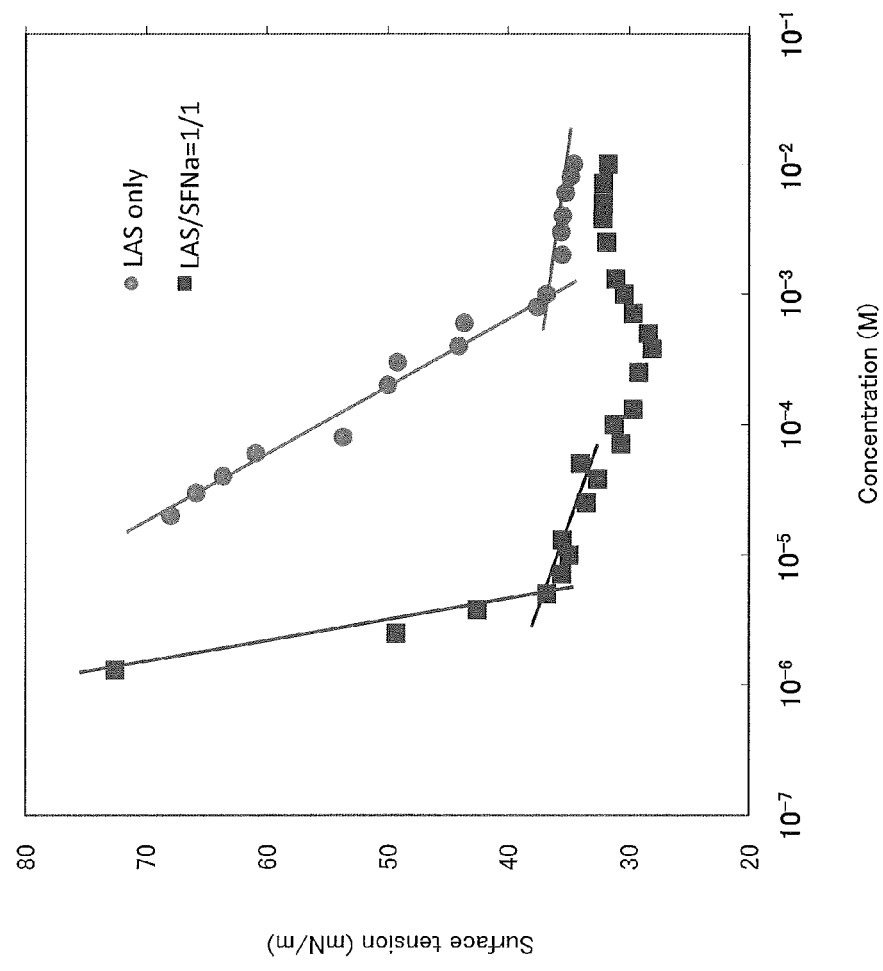
FIG. 1 is a graph to demonstrate the measurement results of the surface tensions of an aqueous solution of sodium linear alkylbenzene sulfonate (LAS) only, and an aqueous solution of LAS and surfactin sodium salt (SFNa) in a molar ratio of 1:1, in other words, an aqueous solution containing 50 mol % of SFNa to the total of LAS and SFNa.

FIG. 1 demonstrates the measurement result of the surface tension of the cases of LAS only and the mixture of LAS and SFNa in 1:1 of molar ratio, in other words, the case where 50 mol % of SFNa is added to a total of LAS and SFNa. It was found by FIG. 1 that when 50 mol % of SFNa is added, an excellent surface tension-lowering ability can be recognized even in a very low concentration in comparison with the case of LAS only.

A surfactant is adsorbed on a surface to reduce surface tension. In addition, after the adsorption becomes saturated, surface tension becomes constant and a surfactant forms an aggregate referred to as micelle in water. A general surfactant forms micelle to exert detergency and solubilization ability to dissolve oil dirt. A concentration at which micelle is formed is referred to as CMC: Critical Micelle Concentration. If CMC is reduced, an amount of a surfactant to be used can be reduced. The CMC values of aqueous solutions of LAS only, the mixture of LAS/SFNa and SFNA only were calculated from the measurement result of surface tension demonstrated in FIG. 1. The values are shown in Table 1.

TABLE 1

|  | CMC (M) | $\gamma_{CMC}$ (mN/m) |
| --- | --- | --- |
| LAS | $1.1 \times 10^{-3}$ | 35.2 |
| LAS/SFNa (1/1) | $4.9 \times 10^{-6}$ | 35.7 |
| SFNa | $2.7 \times 10^{-5}$ | 27.2 |

It was found by the result demonstrated in Table 1 that when 50 mol % of SFNa is added to the total of LAS and SFNa, the critical micelle concentration becomes smaller by about three digit, in other words, is reduced to about 1/1000, in comparison with the case of LAS only. In addition, when 50 mol % of SFNa is added, the CMC becomes smaller by about one digit (1/10) in comparison with the case of SFNa only. It is considered that the result can be obtained by the specific synergistic effect of LAS and SFNa having a bulky peptide structure.

Figure 2:
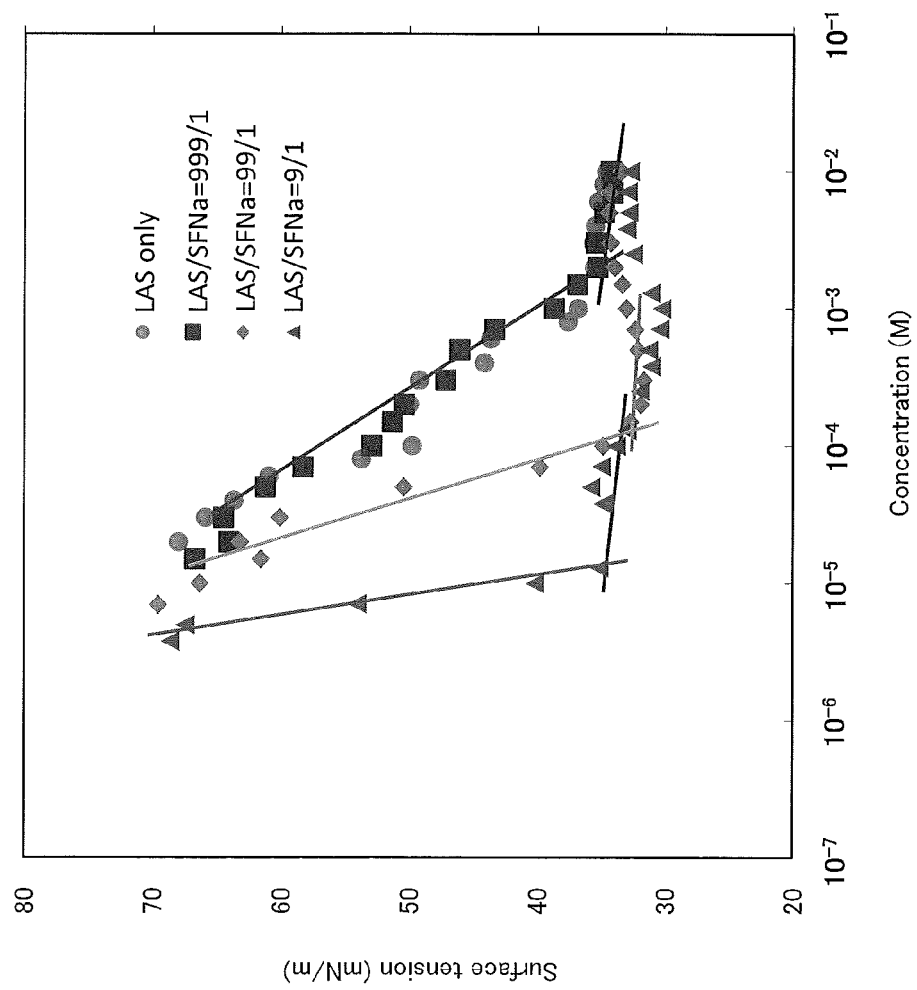
FIG. 2 is a graph to demonstrate the measurement results of the surface tensions of an aqueous solution of LAS only, and aqueous solutions prepared by adding SFNa in a molar ratio of 9:1 (10 mol %), 99:1 (1 mol %) and 999:1 (0.1 mol %) to the total of LAS and SFNa.

FIG. 2 demonstrates the measurement result of surface tension in the case of LAS only and the case where SFNa was added in a molar ratio of 9:1 (10 mol %), 99:1 (1 mol %) or 999:1 (0.1 mol %) to the total of LAS and SFNA. It was confirmed by FIG. 2 that when 0.1 mol % of SFNa is added, the effect to reduce surface tension by LAS cannot be improved, but when 1 mol % and 10 mol % of SFNa is added, the effect to reduce surface tension can be recognized.

The CMC values of each aqueous solution were calculated from the measurement result of surface tension demonstrated in FIG. 2. The values are shown in Table 2.

TABLE 2

|  | CMC (M) | $\gamma_{CMC}$ (mN/m) |
|---|---|---|
| LAS | $1.1 \times 10^{-3}$ | 35.2 |
| LAS/SFNa (999/1) | $2.1 \times 10^{-3}$ | 34.8 |
| LAS/SFNa (99/1) | $1.5 \times 10^{-4}$ | 33.1 |
| LAS/SFNa (9/1) | $1.6 \times 10^{-5}$ | 35.2 |

It was found by the result demonstrated in Table 2 that when 10 mol % of SFNa is added, the CMC of LAS becomes smaller by about two digit, in other words, is reduced to about 1/100. When 1 mol % of SFNa is added, the CMC of LAS becomes smaller by about one digit, in other words, is reduced to about 1/10.

As the above-described results, it was clarified that when SFNa having a bulky cyclic peptide structure is added even in a slight amount, an amount of LAS to be used as a main cleaning ingredient can be considerably reduced.

Example 2: Effect to Reduce Amount of Sodium Dodecyl Sulfate to be Used by Surfactin Sodium Salt Next, the effect to reduce an amount of sodium dodecyl sulfate (SDS) to be used by surfactin sodium salt (SFNa) was evaluated by surface tension measurement. SDS is a major anionic surfactant as LAS. Specifically, similarly to the above-described Example 1 except that SDS was used in place of LAS, aqueous solutions of SDS only, the mixture of SDS/SFNa and SFNa only were prepared and the surface tension was measured. The result is shown in FIG. 3.

Figure 3:
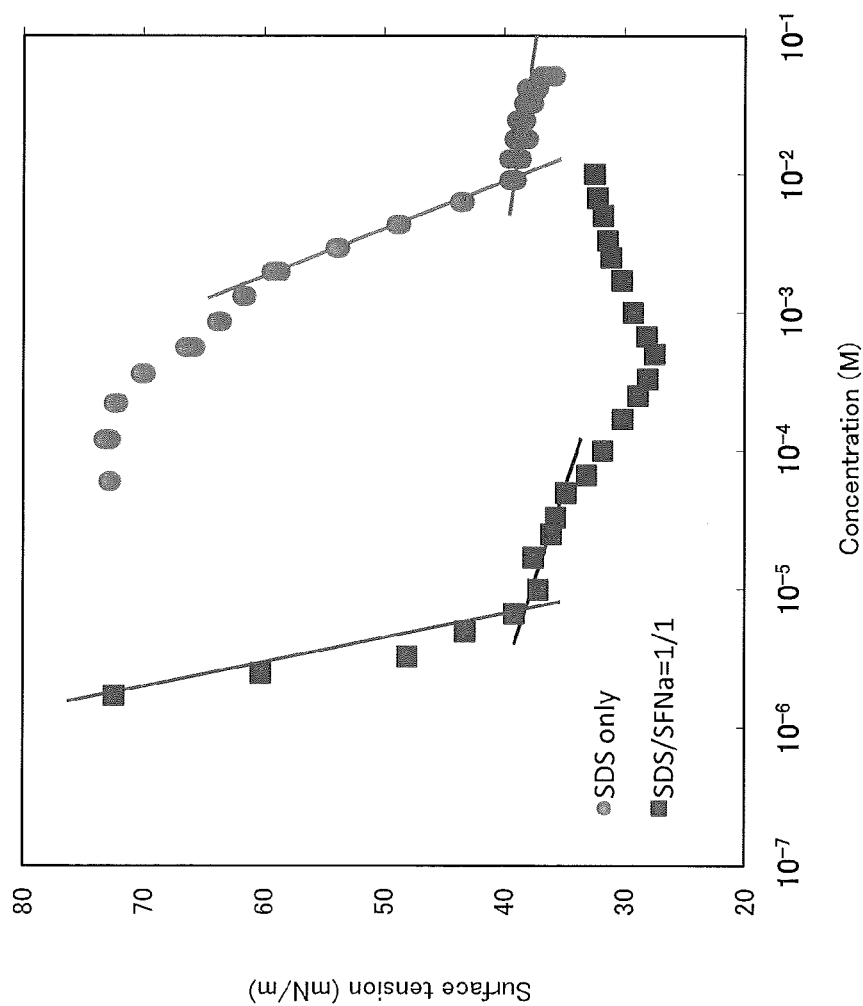
FIG. 3 is a graph to demonstrate the measurement results of the surface tensions of an aqueous solution of sodium dodecyl sulfate (SDS) only, and an aqueous solution prepared by mixing SDS and SFNa in a molar ratio of 1:1, in other words, an aqueous solution containing 50 mol % of SFNa to the total of SDS and SFNa.

It was found by FIG. 3 that when 50 mol % of SFNa is added, an excellent surface tension-lowering ability can be recognized even in a very low concentration in comparison with the case of SDS only. The CMC values of each aqueous solution were calculated from the measurement result of surface tension demonstrated in FIG. 3. The values are shown in Table 3.

TABLE 3

|  | CMC (M) | $\gamma_{CMC}$ (mN/m) |
|---|---|---|
| SDS | $8.4 \times 10^{-3}$ | 39.7 |
| SDS/SFNa (1/1) | $8.2 \times 10^{-6}$ | 36.3 |
| SFNa | $2.7 \times 10^{-5}$ | 27.2 |

It was clarified by the result demonstrated in Table 3 that when 50 mol % of SFNa is added to the total of SDS and SFNa, the critical micelle concentration becomes smaller by about three digit, in other words, is reduced to about 1/1000, similarly to the case of LAS. In addition, when 50 mol % of SFNa was added, the CMC became smaller by about one digit (1/10) in comparison with the case of SFNa only.

Figure 4:
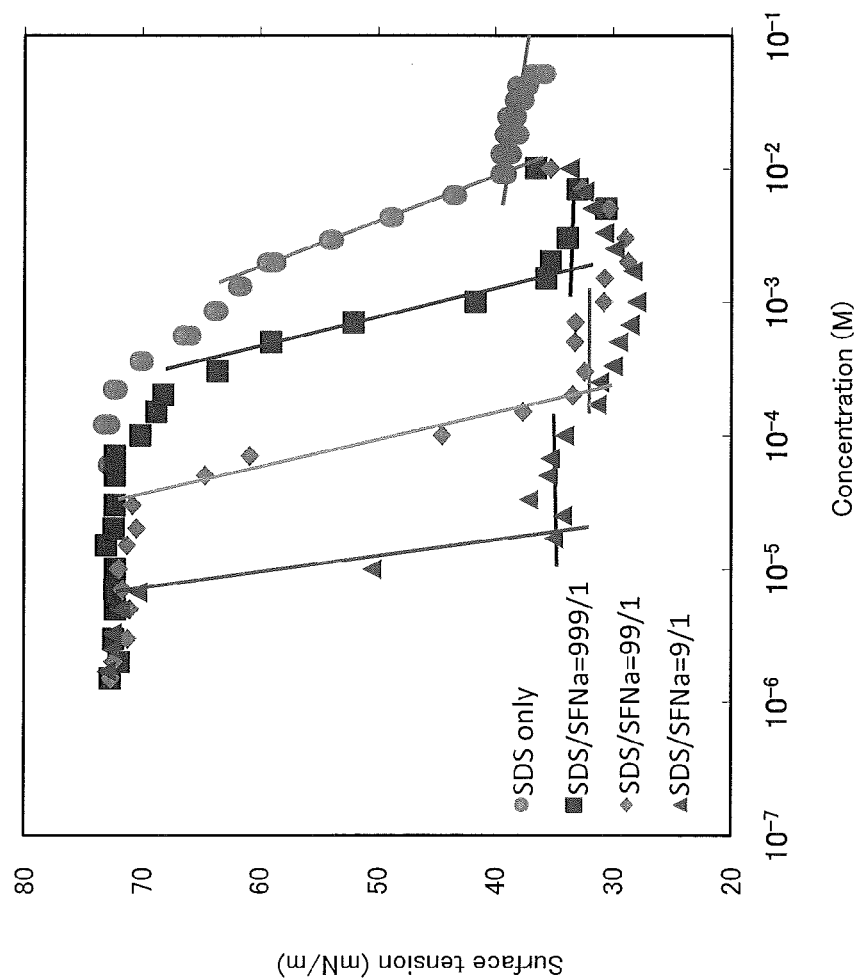
FIG. 4 is a graph to demonstrate the measurement results of the surface tensions of an aqueous solution of SDS only, and aqueous solutions prepared by adding SFNa in a molar ratio of 9:1 (10 mol %), 99:1 (1 mol %) and 999:1 (0.1 mol %) to the total of SDS and SFNa.

FIG. 4 demonstrates the measurement result of surface tension in the case of SDS only and the case where SFNa was added in a molar ratio of 9:1 (10 mol %), 99:1 (1 mol %) or 999:1 (0.1 mol %) to the total of SDS and SFNa. It was confirmed by FIG. 4 that unlike the case of LAS, even when 0.1 mol % of SFNa is added, in other words, even when 1/1000 of SFNa is added to the total of SDS and SFNa, the effect to reduce surface tension can be recognized, and when 1 mol % and 10 mol % of SFNa was added, further remarkable effect to reduce surface tension can be recognized.

The CMC values of each aqueous solution were calculated from the measurement result of surface tension demonstrated in FIG. 4. The values are shown in Table 4.

TABLE 4

|  | CMC (M) | $\gamma_{CMC}$ (mN/m) |
|---|---|---|
| SDS | $8.4 \times 10^{-3}$ | 39.7 |
| SDS/SFNa (999/1) | $1.7 \times 10^{-3}$ | 34.9 |
| SDS/SFNa (99/1) | $2.0 \times 10^{-4}$ | 33.4 |
| SDS/SFNa (9/1) | $1.6 \times 10^{-5}$ | 35.2 |

It was clarified by the result demonstrated in Table 4 that the CMC value of SDS can be reduced by about two digit, i.e. to about 1/100, by addition of 10 mol % of SFNa, by about one digit, i.e. to about 1/10, by addition of 1 mol %, and to a fraction even by addition of 0.1 mol %. As the above-described results, it was clarified that when SFNa having a bulky cyclic peptide structure is added even in a slight amount, an amount of SDS, which is used in a wide range of areas, can be also considerably reduced similarly to the case of LAS.

Reference Example 1: Effect to Reduce Amount of Polyoxyethylene Alkyl Ether to be Used by Surfactin Sodium Salt Next, the effect to reduce the amount of polyoxyethylene alkyl ether (POE-AE) to be used by surfactin sodium salt (SFNa) was evaluated by surface tension measurement similarly to the cases of LAS and SDS. POE-AE is a major non-ionic surfactant. Specifically, similarly to the above-described Example 1 and Example 2 except that POE-AE ("NEWCOL2308" manufactured by NIPPON NYUKAZAI CO., LTD.) was used in place of LAS and SDS, aqueous solutions of POE-AE only, the mixture of POE-AE/SFNa and SFNa only were prepared and the surface tension was measured. The result is shown in FIG. 5.

Figure 5:
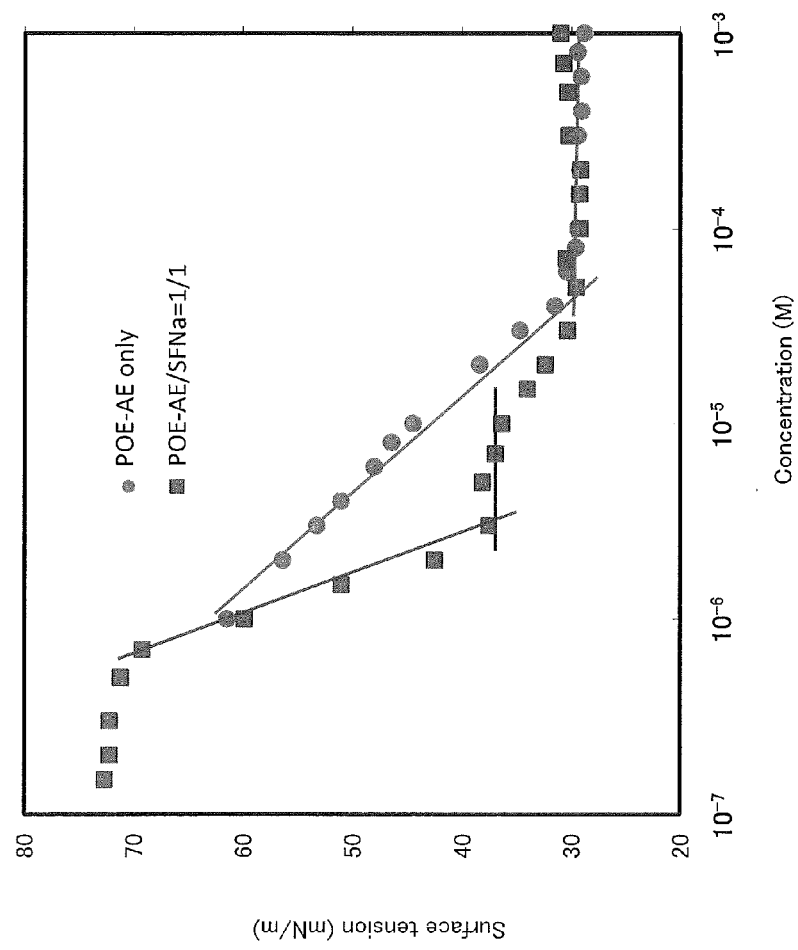
FIG. 5 is a graph to demonstrate the measurement results of the surface tensions of an aqueous solution of a polyoxyethylene alkyl ether (POE-AE) only as a non-ionic surfactant, and an aqueous solution of POE-AE and SFNa in a molar ratio of 1:1, in other words, an aqueous solution containing 50 mol % of SFNa to the total of POE-AE and SFNa.

It was found by FIG. 5 that when 50 mol % of SFNa is added, a surface tension-lowering ability can be recognized even in a low concentration in comparison with the case of POE-AE only; however, the effect was not so much remarkable as that for an anionic surfactant such as LAS and SDS. The CMC values of each aqueous solution were calculated from the measurement result of surface tension demonstrated in FIG. 5. The values are shown in Table 5.

TABLE 5

|  | CMC (M) | $\gamma_{CMC}$ (mN/m) |
|---|---|---|
| POE-AE | $6.8 \times 10^{-5}$ | 29.3 |
| POE-AE/SFNa (1/1) | $2.8 \times 10^{-6}$ | 37.3 |
| SFNa | $2.7 \times 10^{-5}$ | 27.2 |

In the case of LAS and SDS, when 50 mol % of SFNa was added, the critical micelle concentration became smaller by about three digit, in other words, was reduced to about 1/1000. However, when 50 mol % of SFNa was added to the total of POE-AE and SFNa, the critical micelle concentration became smaller by about one digit, in other words, was reduced to about 1/10, in comparison with the case of POE-AE only.

Figure 6:
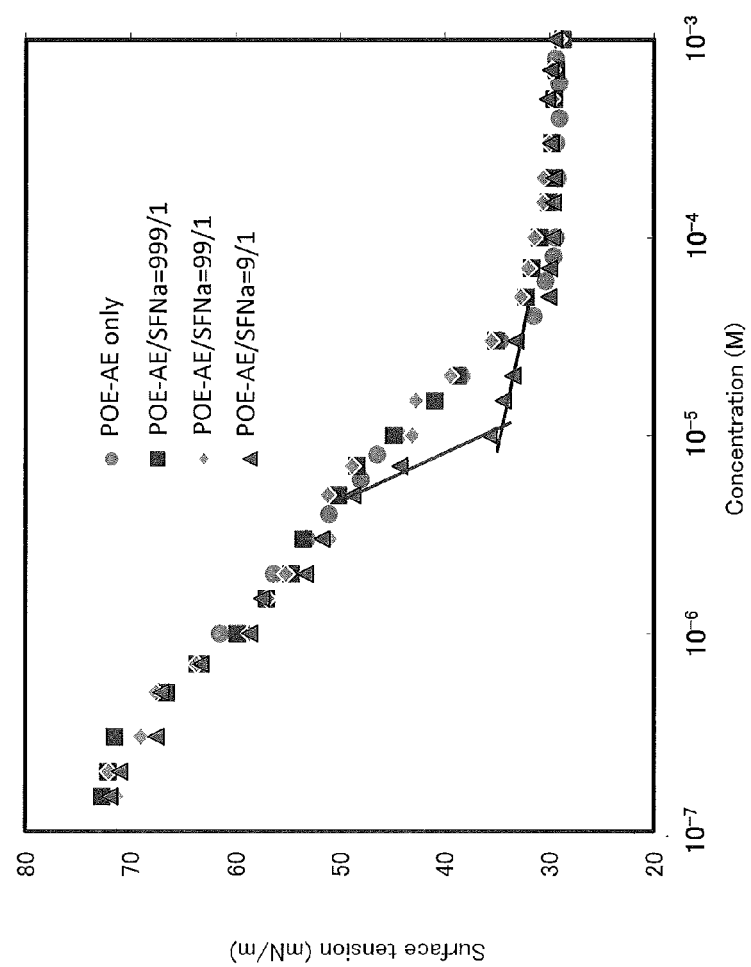
FIG. 6 is a graph to demonstrate the measurement results of the surface tensions of an aqueous solution of POE-AE only, and aqueous solutions prepared by adding SFNa in a molar ratio of 9:1 (10 mol %), 99:1 (1 mol %) and 999:1 (0.1 mol %) to the total of POE-AE and SFNa.

FIG. 6 demonstrates the measurement result of surface tension in the case of POE-AE only and the case where SFNa was added in a molar ratio of 9:1 (10 mol %), 99:1 (1 mol %) or 999:1 (0.1 mol %) to the total of POE-AE and SFNa. It was confirmed by FIG. 6 that unlike the cases of LAS and SDS, only when 10 mol % of SFNa is added to the total of POE-AE and SFNa, the effect to reduce surface tension can be recognized; on the one hand, when 0.1 mol % and 1 mol % of SFNa is added, the effect to reduce surface tension cannot be recognized.

The CMC values of each aqueous solution were calculated from the measurement result of surface tension demonstrated in FIG. 6. The values are shown in Table 6.

TABLE 6

|  | CMC (M) | $\gamma_{CMC}$ (mN/m) |
|---|---|---|
| POE-AE | $6.8 \times 10^{-5}$ | 29.3 |
| POE-AE/SFNa (999/1) | $6.5 \times 10^{-5}$ | 30.3 |
| POE-AE/SFNa (99/1) | $6.8 \times 10^{-5}$ | 30.7 |
| POE-AE/SFNa (9/1) | $1.8 \times 10^{-5}$ | 34.3 |

It was clarified by the result demonstrated in Table 6 that when 10 mol % of SFNa is added, the CMC value of POE-AE can be reduced by about ¼; however, when 0.1 mol % and 1 mol % of SFNa is added, the CMC value is not reduced in comparison with the case of POE-AE only.

It was clarified by the above result that the effect to reduce an amount of a non-ionic surfactant by SFNa having a cyclic peptide structure can be recognized; however, the effect is not so much remarkable as the case of an anionic surfactant.

Figure 7:
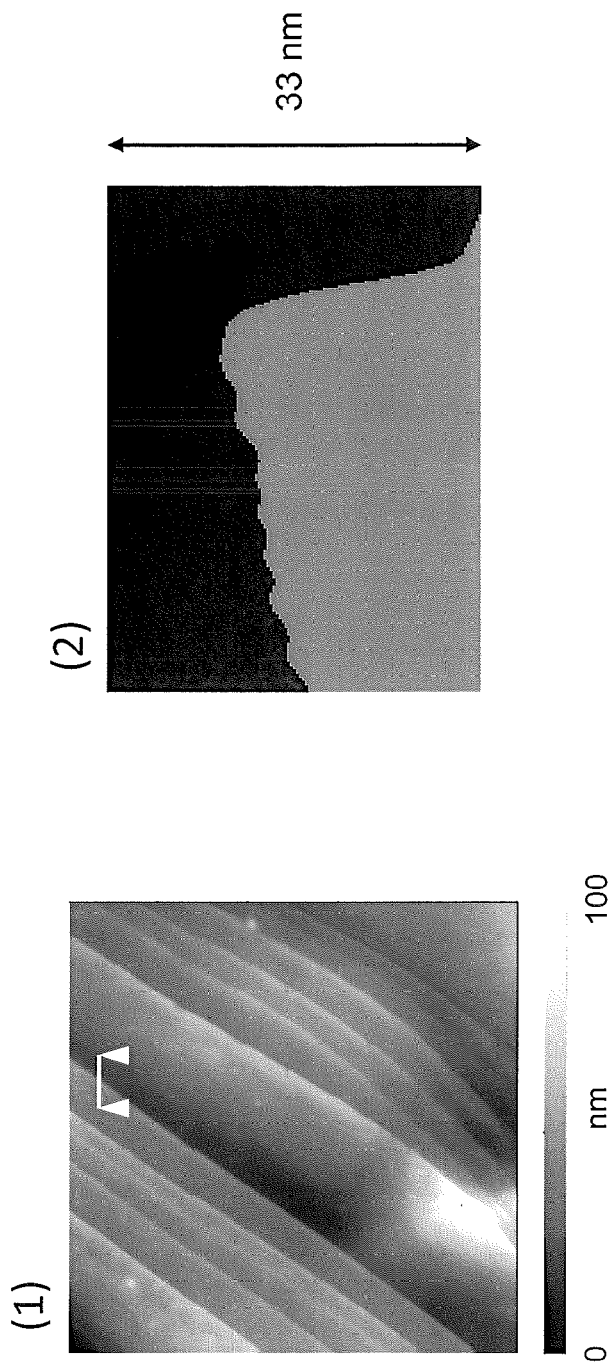
FIG. 7 are photographs of a membrane formed by SFNa using an atomic force microscope. (1) is a two-dimensional shape image, and (2) represents a thickness of the layer.

Reference Example 2: Orientation of Surfactin Sodium Salt on Solid Base Material SFNa and ultrapure water were weighed so that the concentration became 1 mM in a vial container, and SFNa was dissolved by stirring with a stirrer. A drop of the solution was added on a mica base material using a Pasteur pipette, and dried in air at room temperature. The surface of the mica base material on which SFNa was oriented was observed using an atomic force microscope ("SPI4000" manufactured by Seiko Instruments Inc.). The result is shown in FIG. 7. In FIG. 7(1), the scale under the photograph represents the relation between the color in the photograph and the height in the longitudinal direction.

As FIG. 7, it was observed that a characteristic layer structure was formed on the mica surface in a scale of 5 μm×5 μm. The result was derived from the association of SFNa to form the layer structure. The thickness of the layer was about 30 nm, and sufficiently longer than the molecular length of SFNa, i.e. about 2.5 nm. It was therefore clarified that the multi-layer structure was formed by a plurality of SFNa molecule. It is considered that the hydrophilic bulky cyclic peptide part of SFNa adsorbs onto the surface of mica, since the surface of mica is hydrophilic. Even a small amount of SFNa can reform the surface of a solid, since the cyclic peptide part of SFNa is very bulky and the occupancy area by the molecule thereof is very large. Further, it is considered that the property of other surfactant can be dramatically improved by adding even a small amount of SFNa, since SFNa has excellent orientation property.

Figure 8:
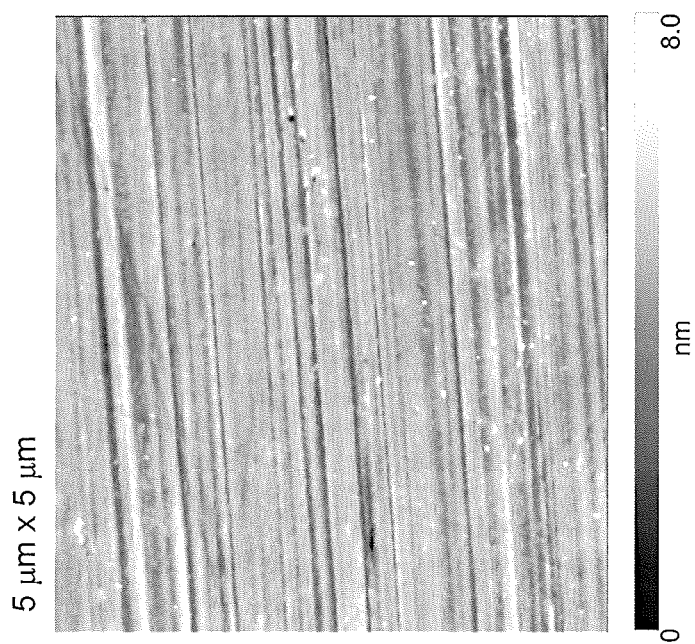
FIG. 8 is a photograph of the surface of a SUS base material using an atomic force microscope.
Figure 9:
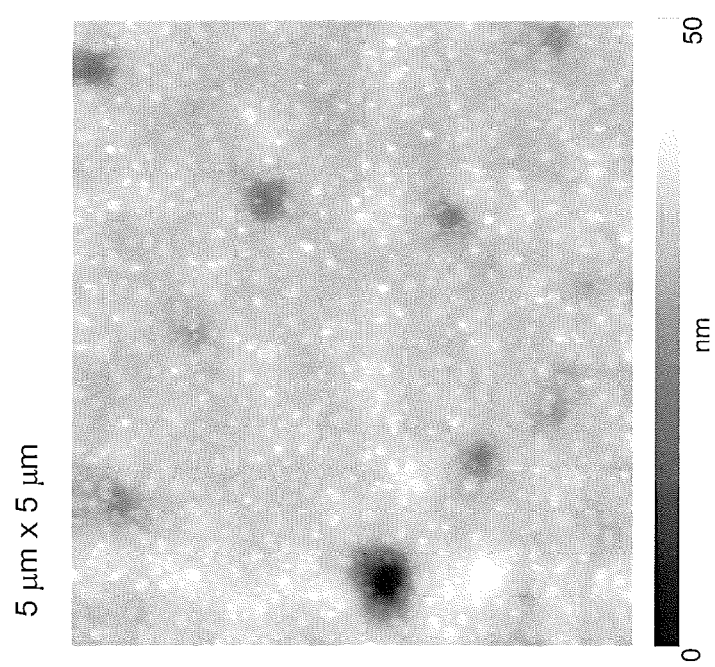
FIG. 9 is a photograph of a membrane formed by SFNa on a SUS base material using an atomic force microscope.

Reference Example 3: Formation of Coat by Surfactin Sodium Salt on Solid Base Material SFNa and ultrapure were weighed so that the concentration became 1 mM, i.e. 1000 ppm, in a vial container, and SFNa was dissolved by stirring with a stirrer. A drop of the solution was added on a SUS base material which was subjected to precision polishing treatment ("SUS304" manufactured by Ultra Finish Technology Co., Ltd.) using a Pasteur pipette, and dried in a desiccator. The surface of the SUS base material was observed using an atomic force microscope ("SPI4000" manufactured by Seiko Instruments Inc.) in a tapping mode. The SUS base material before being treated by the SFNa solution was similarly observed for comparison. The atomic force microscope photograph of the SUS base material is shown as FIG. 8, and the atomic force microscope photograph of the SUS base material treated by the SFNa solution is shown as FIG. 9. In FIGS. 8 and 9, the scale under the photographs represents the relation between the color in the photograph and the height in the longitudinal direction.

As FIG. 8, the existence of asperity due to polishing was observed on the surface of the SUS base material before being treated by the SFNa solution. The size of the asperity was about several nanometers. On the one hand, as FIG. 9, asperity could be hardly recognized on the SUS base material treated by the SFNa solution and it was observed that SFNa associated to form the layer structure. Thus, it could be confirmed that SFNa also forms coat on a SUS base material.

Figure 10:
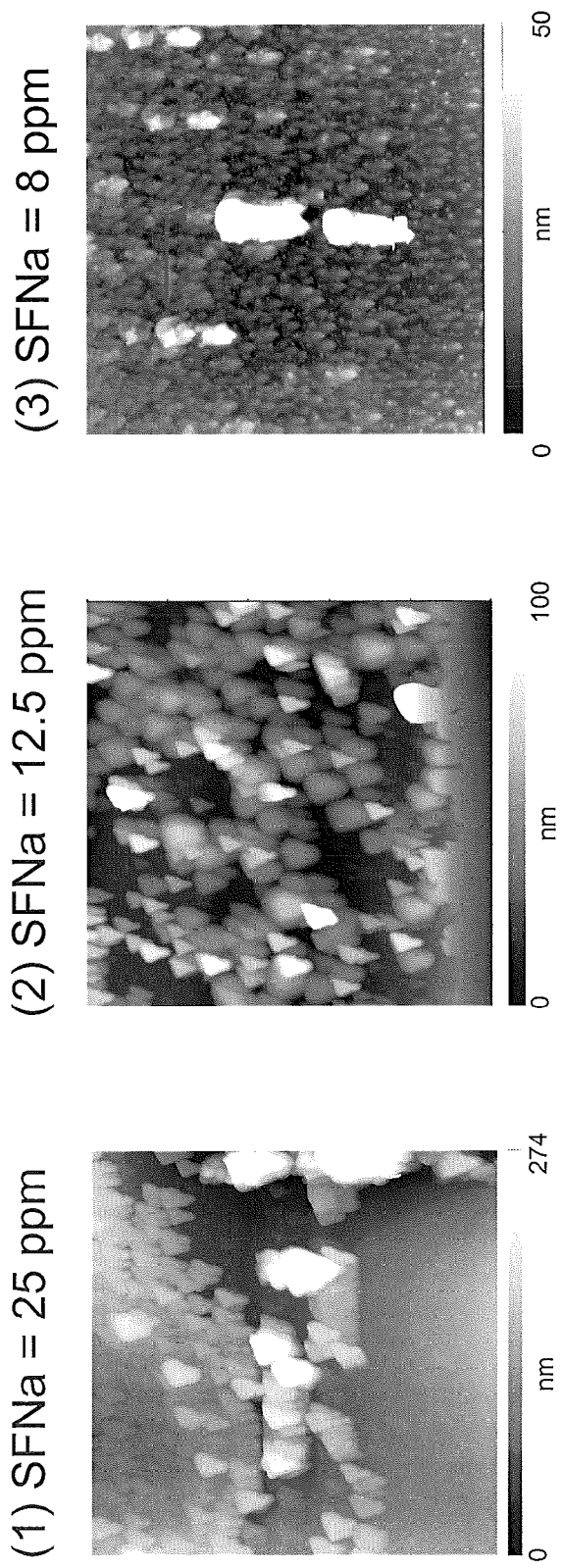
FIG. 10 are photographs of membranes formed by SFNa on a SUS base material using an atomic force microscope.

Reference Example 4: Formation of Coat by Surfactin Sodium Salt on Solid Base Material SFNa and ultrapure were weighed so that the concentration became 0.025 mM (25 ppm), 0.0125 mM (12.5 ppm) or 0.008 mM (8 ppm) in a vial container, and SFNa was dissolved by stirring with a stirrer. A drop of each solution was added on a SUS base material which was subjected to precision polishing treatment ("SUS304" manufactured by Ultra Finish Technology Co., Ltd.) using a Pasteur pipette, and dried in a desiccator. The surface of each base material was observed using an atomic force microscope in a tapping mode similarly to the above-described Reference example 3, and the photographs of the surfaces were taken. Each photograph is shown as FIGS. 10(1) to (3). In FIG. 10, the scale under each photograph represents the relation between the color in the photograph and the height in the longitudinal direction.

As FIG. 10(1), on the SUS surface treated by 25 ppm SFNa aqueous solution, the asperity which was on the SUS base material of FIG. 8 could not be observed but the formation of a characteristic coat could be observed. The result was derived from the association of SFNa on the base material to form the layer structure. In addition, as FIGS. 10(2) and (3), the formation of similar coat was observed on the SUS surface treated by the SFNa solutions having lower concentration as 12.5 ppm and 8 ppm. Thus, even a small amount of SFNa can reform the surface of a solid, since the cyclic peptide part of SFNa is very bulky and the occupancy area by the molecule thereof is very large. Further, it is considered that the property of other surfactant can be dramatically improved by adding even a small amount of SFNa, since SFNa has excellent orientation property.

Example 3: Effect to Reduce Amount of Sodium Perfluorooctanoate to be Used by Surfactin Sodium Salt Similarly to the cases of sodium linear alkylbenzene sulfonate (LAS) used in the above-described Example 1 and sodium dodecyl sulfate (SDS) used in the above-described Example 2, the effect to reduce the amount of sodium perfluorooctanoate (PFOSNa) to be used by surfactin sodium salt (SFNa) was evaluated by surface tension measurement. There is concerned that PFOSNa negatively affects the environment.

A PFOSNa aqueous solution was prepared by neutralizing perfluorooctanoic acid (PFOS) manufactured by TOHKEM PRODUCTS CORPORATION with a sodium hydroxide aqueous solution. Similarly to the above-described Example 1 and Example 2 except that PFOSNa was used in place of LAS and SDS, aqueous solutions of PFOSNa only, the mixture of PFOSNa/SFNa and SFNa only were prepared and the surface tension was measured. The result is shown in FIG. 11.

It was found by FIG. 11 that when 50 mol % of SFNa is added, an excellent surface tension-lowering ability can be recognized even in a very low concentration in comparison with the case of PFOSNa only. The CMC values of each aqueous solution were calculated from the measurement result of surface tension demonstrated in FIG. 11. The values are shown in Table 7.

TABLE 7

|  | CMC (M) | $\gamma_{CMC}$ (mN/m) |
|---|---|---|
| PFOSNa | $2.0 \times 10^{-3}$ | 43.4 |
| PFOSNa/SFNa (1/1) | $9.1 \times 10^{-6}$ | 35.3 |
| SFNa | $2.7 \times 10^{-5}$ | 27.2 |

It was found by the result demonstrated in Table 7 that when 50 mol % of SFNa is added to the total of PFOSNa and SFNa, the critical micelle concentration becomes smaller by about three digit, in other words, is reduced to about 1/1000, in comparison with the case of PFOSNa only similarly to the cases of LAS and SDS. In addition, when 50 mol % of SFNa was added, the CMC became smaller in comparison with the case of SFNa only.

FIG. 12 demonstrates the measurement result of surface tensions in the case of PFOSNa only and the case where SFNa was added in a molar ratio of 9:1 (10 mol %), 99:1 (1 mol %) or 999:1 (0.1 mol %) to PFOSNa. It was confirmed by FIG. 12 that the effect to reduce surface tension can be recognized in all of the cases, and when 10 mol % of SFNa is added, further remarkable effect to reduce surface tension can be recognized.

The CMC values of each aqueous solution were calculated from the measurement result in FIG. 12. The values are shown in Table 8.

TABLE 8

|  | CMC (M) | $\gamma_{CMC}$ (mN/m) |
|---|---|---|
| PFOSNa | $2.0 \times 10^{-3}$ | 43.4 |
| PFOSNa/SFNa (999/1) | $2.0 \times 10^{-3}$ | 32.6 |
| PFOSNa/SFNa (99/1) | $9.5 \times 10^{-4}$ | 32.4 |
| PFOSNa/SFNa (9/1) | $2.8 \times 10^{-5}$ | 32.2 |

It was clarified by the result demonstrated in Table 8 that when 10 mol % of SFNa is added, the CMC value of PFOSNa becomes smaller by about two digit, in other words, is reduced to about 1/100. As the above-described results, it was clarified that when SFNa having a bulky cyclic peptide structure is added, an amount of PFOSNa, of which influence on the environment is worried, can be also considerably reduced.

Example 4: Effect to Reduce Amount of Sodium Laurate to be Used by Surfactin Sodium Salt The effect to reduce an amount of sodium laurate (LaNa) to be used by surfactin sodium salt (SFNa) was evaluated by surface tension measurement. Specifically, using LaNa (manufactured by Wako Pure Chemical Industries, Ltd.), surface tensions of aqueous solutions were measured in the case of LaNa only and the cases where SFNa was added to LaNa in a molar ratio of 9:1 (10 mol %), 99:1 (1 mol %) or 999:1 (0.1 mol %). The result is shown in FIG. 13.

It was confirmed by FIG. 13 that when 0.1 mol % and 1 mol % of SFNa is added, the surface tension is nearly the same as the case of LaNa only; but when 10 mol % of SFNa is added, the effect to reduce surface tension can be recognized. In addition, when 0.1 mol % and 1 mol % of SFNa was added, the surface tension continued to be moderately reduced in the range of measurement concentration similarly to the case of LaNa only. It was therefore found that the critical micelle concentrations of the solutions are $1.0 \times 10^{-2}$ M or more. On the one hand, as FIG. 13, it was found that when 10 mol % of SFNa is added to LaNa, the critical micelle concentration is $1.5 \times 10^{-5}$ M. The CMC value is smaller by at least about three digit, in other words, is reduced to about 1/1000, in comparison with the case of LaNa only similarly to the cases of LAS and SDS. As the above-described results, it was confirmed that when SFNa having a bulky cyclic peptide structure is added, an amount of LaNa can be also considerably reduced.

Example 5: Confirmation of Mixed Micelle Formation by Surfactin Sodium Salt and Sodium Linear Alkylbenzene Sulfonate (LAS)

In the mixture prepared by adding surfactin sodium salt (SFNa) to a sodium linear alkylbenzene sulfonate (LAS), the formation of micelle was actually determined at a low concentration. Specifically, an aqueous solution of LAS only was prepared and an aqueous solution was prepared by adding SFNa to LAS in a molar ratio of 9:1 (10 mol %) similarly to the above-described Example 1. The scattered light intensity of prepared aqueous solutions having each concentration was measured using a light scattering photometer ("DLS-7000" manufactured by Otsuka Electronics Co., Ltd.). In the measurement, Ar laser ($\lambda$=488 nm) was used as a light source and scattering angle was set to 90°. The relative scattered light intensities were plotted against the concentrations. The relative scattered light intensity is a ratio of the measured scattered light intensity to the scattered light intensity of ultrapure water as a solvent. The result is shown as FIG. 14.

While a relative scattered light intensity is generally increased with the formation of micelle, it was confirmed as FIG. 14 that when 10 mol % of SFNa is added, a relative scattered light intensity is drastically increased even at a lower concentration by about two digit, i.e. about 1/100, in comparison with the case of LAS only. The concentration at which a scattered light intensity was increased in the case where 10 mol % of SFNa was added agreed well with the critical micelle concentration obtained by the surface tension measurement of the above-described Example 1. It was clarified from the results that micelle can be actually formed even at a low concentration by adding SFNa having a bulky peptide structure.

Example 6: Effect to Reduce Amount of Sodium Linear Alkylbenzene Sulfonate to be Used for Emulsification by Surfactin Sodium Salt In the mixture prepared by adding surfactin sodium salt (SFNa) to a sodium linear alkylbenzene sulfonate (LAS), the ability to emulsify squalane at a low concentration was evaluated. Specifically, similarly to the above-described Example 1, aqueous solutions having a total surfactant concentration of $1.5 \times 10^{-5}$ M were prepared. In the aqueous solutions, the surfactant was LAS only, SFNa only, or the mixture prepared by adding SFNa to LAS in a molar ratio of 9:1 (10 mol %). In addition, ultrapure water only to which a surfactant was not added was also prepared as a control. Into a test tube, 1 mL of the aqueous solution or ultrapure water and 3 mL of squalane (manufactured by Wako Pure Chemical Industries, Ltd.) were added. The mixture was stirred using a Vortex mixer for 1 minute. The solutions were allowed to stand still at 25° C. for 1 day and observed visually. The result is shown in FIG. 15.

As FIG. 15, when 10 mol % of SFNa was added to LAS, an emulsion in which squalane and water were emulsified was obtained. After 1 day, the emulsion was stable. On the one hand, in the cases of LAS ($1.5 \times 10^{-6}$ M) only and SFNa ($1.4 \times 10^{-5}$ M) only, a stable emulsion could not be obtained as a system containing no surfactant, and an aqueous phase and an oil phase were separated from each other. As the above-described results, it was clarified that when SFNa having a bulky cyclic peptide structure is added, an amount of LAS to be used can be actually reduced to a large degree.

The invention claimed is:

1. A method for reducing a critical micelle concentration of an anionic surfactant, comprising:
    mixing a cyclic lipopeptide biosurfactant with the anionic surfactant.

2. The method according to claim 1, wherein surfactin represented by the following formula (I) or a salt thereof is used as the cyclic lipopeptide biosurfactant:

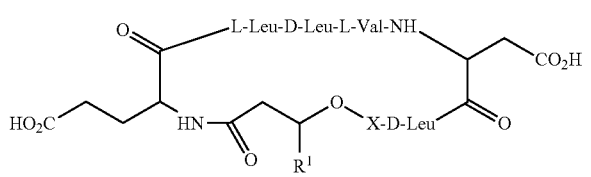

(I)

wherein 'X' is a residue of amino acid selected from leucine, isoleucine and valine; and $R^1$ is a $C_{9-18}$ alkyl group.

3. The method according to claim 1, wherein a linear alkylbenzene sulfonate, an alfa-olefin sulfonate or an alkyl sulfate is used as the anionic surfactant.

4. The method according to claim 1, wherein the cyclic lipopeptide biosurfactant is used in a ratio of 0.1 mol % or more to a total of the anionic surfactant and the cyclic lipopeptide biosurfactant.

5. A surfactant composition, comprising an anionic surfactant and a cyclic lipopeptide biosurfactant.

6. The surfactant composition according to claim 5, wherein the cyclic lipopeptide biosurfactant is surfactin represented by the following formula (I) or a salt thereof:

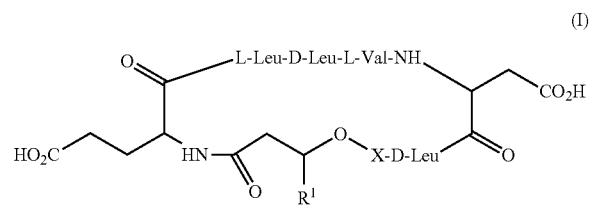

(I)

wherein 'X' is a residue of amino acid selected from leucine, isoleucine and valine; and $R^1$ is a $C_{9-18}$ alkyl group.

7. The surfactant composition according to claim 5, wherein the anionic surfactant is a linear alkylbenzene sulfonate, an alfa-olefin sulfonate or an alkyl sulfate.

8. The surfactant composition according to claim 5, comprising the cyclic lipopeptide biosurfactant in a ratio of 0.1 mol % or more to a total of the anionic surfactant and the cyclic lipopeptide biosurfactant.

9. The surfactant composition according to claim 5, further comprising water.

10. The method according to claim 1, wherein a synthetic anionic surfactant is used as the anionic surfactant.

11. The surfactant composition according to claim 5, wherein the anionic surfactant is a synthetic anionic surfactant.

12. The method according to claim 1, wherein the cyclic lipopeptide biosurfactant is added to the anionic surfactant.

\* \* \* \* \*